United States Patent
Leboudec (10) Patent No.: US 11,630,117 B2
(45) Date of Patent: Apr. 18, 2023

(54) MONITORING A LABORATORY AUTOMATION DEVICE VIA A SIMULATION MODEL

(71) Applicant: TECAN TRADING AG, Maennedorf (CH)

(72) Inventor: Ronan Leboudec, Zurich (CH)

(73) Assignee: TECAN TRADING AG, Switzerland (CH)

( * ) Notice: Subject to any disclaimer, the term of this patent is extended or adjusted under 35 U.S.C. 154(b) by 1107 days.

(21) Appl. No.: 16/213,787

(22) Filed: Dec. 7, 2018

(65) Prior Publication Data

US 2019/0195903 A1 Jun. 27, 2019

(30) Foreign Application Priority Data

Dec. 21, 2017 (EP) ..................... 17209257

(51) Int. Cl.
*G06F 30/33* (2020.01)
*G01N 35/00* (2006.01)
(Continued)

(52) U.S. Cl.
CPC ....... *G01N 35/00722* (2013.01); *G01N 33/53* (2013.01); *G01N 35/0092* (2013.01);
(Continued)

(58) Field of Classification Search
CPC ............. G01N 35/00722; G01N 33/53; G01N 35/00871; G01N 35/0092;
(Continued)

(56) References Cited

U.S. PATENT DOCUMENTS

| 6,721,615 B2 * | 4/2004 | Fava | G05B 19/41865 |
| | | | 700/99 |
| 8,747,746 B2 * | 6/2014 | Lefebvre | G01N 1/312 |
| | | | 422/65 |

(Continued)

FOREIGN PATENT DOCUMENTS

| CN | 106457250 A | * | 2/2017 | .............. B01L 3/02 |
| CN | 104204812 B | * | 1/2018 | .............. C12Q 1/68 |

(Continued)

OTHER PUBLICATIONS

Satoshi Saitoh et al.; "Fully Automated Laboratory Robotic System for Automating Sample Preparation and Analysis to Reduce Cost and Time in Drug Development"; 2008 by The Association for Laboratory Automation (Year: 2008).*

(Continued)

*Primary Examiner* — Rehana Perveen
*Assistant Examiner* — Nupur Debnath
(74) *Attorney, Agent, or Firm* — MH2 Technology Law Group LLP (57) ABSTRACT

A laboratory automation device (10) includes a plurality of device components (14, 16), which are controlled by digital control commands (26). The digital control commands (26) are generated by a controller (20) of the laboratory automation device (10) from assay definition data (38) defining an assay procedure for the laboratory automation device (10).

20 Claims, 4 Drawing Sheets

(51) Int. Cl.
  *G05B 17/02* (2006.01)
  *G06F 30/20* (2020.01)
  *G01N 33/53* (2006.01)

(52) U.S. Cl.
  CPC ....... *G01N 35/00871* (2013.01); *G05B 17/02* (2013.01); *G06F 30/20* (2020.01); *G06F 30/33* (2020.01); *G01N 2035/0097* (2013.01); *G01N 2035/00653* (2013.01)

(58) Field of Classification Search
  CPC . G01N 2035/00653; G01N 2035/0097; G01N 35/00584; G05B 17/02; G06F 30/20; G06F 30/33
  See application file for complete search history.

(56) References Cited

U.S. PATENT DOCUMENTS

| | | | |
|---|---|---|---|
| 10,002,678 B2* | 6/2018 | Dambra | G16H 40/40 |
| 2007/0174653 A1* | 7/2007 | Berman | G01N 35/00623 |
| | | | 714/2 |
| 2014/0094971 A1* | 4/2014 | Thieme | G05B 19/02 |
| | | | 700/275 |
| 2015/0242395 A1 | 8/2015 | Hodak | |

FOREIGN PATENT DOCUMENTS

| | | |
|---|---|---|
| EP | 2918378 A1 | 3/2015 |
| EP | 3195990 A1 | 1/2017 |
| WO | 2016/207886 A2 | 12/2016 |
| WO | WO-2017173380 A1 * | 10/2017 ....... G01N 35/00623 |

OTHER PUBLICATIONS

Bakan Ebubekir et a.; "Automation in the clinical laboratory: integration of several analytical and intra-laboratory pre- and post-analytical systems"; Turkish Journal of Biochemistry (Year: 2016).*
Edward Ki Yun Leung; "The Trials of Implementing Lab Automation Systems: Key Lessons from University of Chicago Medical Center's Experience"; (Year: 2017).*
Jan S. Krouwer; "Setting Performance Goals and Evaluating Total Analytical Error for Diagnostic Assays"; Clinical Chemistry 48:6 919-927 (2002) (Year: 2002).*
Rafael Garcia Secundo; "Analysis and Implementation of Laboratory Automation System"; Thesis submitted to the MIT Sloan School of Management (Year: 2015).*
Extended European Search Report dated Jun. 29, 2018 in corresponding European Application No. 17209257.9.
Vogt, Wolfgang, "Realistic Modeling of Clinical Laboratory Operation by Computer Simulation," Clin. Chem.40/6, Laboratory Management and Utlization, 922-928 (1994).

* cited by examiner

| | | | |
|---|---|---|---|
| P | S→W | 25µL | ← 52 |
| P | EC→W | 100µL | ← 52 |
| M | 10s | | ← 52 |
| I | 1h | 37°C | ← 52 |
| W | WB→W | 250µL | ← 52 |

MONITORING A LABORATORY AUTOMATION DEVICE VIA A SIMULATION MODEL

FIELD OF THE INVENTION

The invention relates to a method, a computer program and a computer-readable medium for monitoring a laboratory automation device as well as to a monitoring system.

BACKGROUND OF THE INVENTION

Laboratory automation devices are used for automating task of a laboratory assistant, which, for example, tests a patient for specific diseases. Usually, a sample of the patient's blood, urine, stool, etc. is taken and analysed by means of a bio-chemical procedure. Such a procedure consists in various operations like adding substances, incubating, separating etc. and a measurement process which quantitatively or qualitatively measures the amount or presence of a substance indicating the specific disease. Such an analysis is usually called an assay. The sequence of the steps to be executed is called assay protocol.

All steps of such an assay protocol may be automatically performed by the laboratory automation device. For example, EP 2 918 378 A1 describes such a device.

Laboratory automation devices are usually controlled by an external controller, such as a PC, which is connected via a communication line with the laboratory automation device. Based on a program, the controller controls the laboratory automation device via firmware commands. Some controllers are adapted for translating an assay protocol into a program for controlling the laboratory automation device. This may help to automate the execution of an assay. Assay definition data, encoding the assay may be defined or provided to the controller, which then may translate the assay into the program.

The program generated from the assay definition data may be encoded on a rather high level and may be translated via several intermediate layers, for example by a hardware abstraction layer and by device drivers, into firmware commands, which are then sent to the laboratory automation device.

DESCRIPTION OF THE INVENTION

The multiple translation steps of the assay into the firmware commands may result in unexpected behaviour, which may have to be checked by a human operator. It is an objective of the invention to provide a more secure and more reliable laboratory automation device. A further objective of the invention is to provide an independent monitoring system, which monitors, whether an assay is executed by the laboratory automation device in the intended way.

These objectives are achieved by the subject-matter of the independent claims. Further exemplary embodiments are evident from the dependent claims and the following description.

A first aspect of the invention relates to a method for monitoring a laboratory automation device. The method may be performed automatically by a computing device, which is communicatively interconnected with a controller of the laboratory automation device. Alternatively, the controller itself may automatically perform the method.

According to an embodiment of the invention, the laboratory automation device comprises a plurality of device components, which are controlled by digital control commands, wherein the digital control commands are generated by a controller of the laboratory automation device from assay definition data defining an assay procedure for the laboratory automation device. A device component may be any component of the laboratory automation device which states may be affected by digital control commands. This includes directly controllable components, such as motors, heaters, etc. and indirectly controllable or passive components, such as grippers, pipettes, reagent tubes, etc. It has to be noted that also cavities, which may be filled with a substance or not, or liquid levels in such a cavity may be seen as device components. Furthermore, controllable states may include a position and/or orientation of a component, a liquid level, a temperature, etc.

For example, the device components comprise at least one of an instrument arm, a turntable, a gripper, a pipette, a sensor tip, a plate with wells (i.e. a microplate), a cavity, a well, a plunger, a heating device, etc. Each of the instrument arm, turntable, gripper, pipette, sensor tip and plunger may be moved by one or more motors. A microplate or microtiter plate may be a plate, usually made of plastics, which comprises a plurality of wells aligned in a symmetric grid.

The digital control commands may be or may comprise firmware commands for component controllers of the laboratory automation device. For example, a control command may command a motor to rotate by some steps or may command a gripper and/or pipette to move for some distance in some direction. A control command also may command a heater to heat to a specific temperature. It has to be noted that the digital control command may be provided in a stream and/or series of control commands, which are generated in a specific order and/or which are processed in a specific order.

The control commands are generated from assay definition data. Assay definition data may be stored in a file and/or may encode the steps for processing a sample without specific commands how the steps may be achieved. For example, assay definition data may comprise "add reagent X to sample", but may not comprise the movements of a pipette, how this may be achieved. In general, assay definition data may encode states to be achieved and/or state changes of device components.

The controller may comprise software modules, which translate the assay definition data into hardware independent program commands, which may be translated from further software components, such as drivers into the digital control commands.

According to an embodiment of the invention, the method comprises: receiving the control commands; inputting the control commands into a simulation model of the laboratory automation device, the simulation model comprising model components for at least some of the device components; and updating the simulation model by simulating state changes of the device components based on the control commands. The control commands are not only received by the laboratory automation device, but additionally by a monitoring software module, which uses the control commands for updating a simulation model at least some of the device components.

The simulation model is composed of model components, which represent "real" device components of the laboratory automation device. For example, a pipette may be represented by a 3D-coordinate of its tip and control commands for moving a pipette are translated into a change of the 3D coordinate. Furthermore, the model component for the pipette may comprise a code encoding the actual content of the pipette, such as "empty", "reagent X", "sample X", etc.

Whenever the control commands move the tip of the pipette into a cavity containing a specific substance, which may be seen in the simulation model by checking, whether the tip is inside a 3D-volume representing the cavity, and a control command for filling the pipette is received, then the code for the actual content may be updated.

In general, a model component for a device component may contain codes and/or values of all states, which are modelled by the model component. In particular, these states may comprise a position and/or an orientation, a content, a temperature, an indicator for a state change (such as "heated", "shaked", etc.). The simulation model receives control commands, may associate them with specific model components and/or may update states of the model components as demanded by the control commands. Thus, the received control commands may be translated into changes of codes and/or values of model components.

According to an embodiment of the invention, the method further comprises: determining a desired processing state of the laboratory automation device from the assay definition data and a virtual processing state of the laboratory automation device from the updated simulation model; and comparing the desired processing state with the virtual processing state for deciding, whether the assay procedure was correctly executed. The software module running the simulation model also may receive the assay definition data from the controller of the laboratory automation device. From the assay definition data, the software module may determine, which processing states should be achieved by the laboratory automation device. These processing states are called desired processing states. For example, the assay definition data may encode that a sample should be mixed with a specific reagent. The software module then may determine the state "sample and specific reagent contained in cavity" from this.

On the other hand, the software module may determine the same processing states from the simulation model, when it has been updated by the control commands. These processing states are called virtual processing states. It has to be noted that only a subset of the states, which are simulated by the simulation model, may be included into the virtual processing states. For example, the positions of different samples, which have been mixed with specific reagents, are not of interest, but only the specific reagents.

The desired processing states and the virtual processing states may be comparable, i.e. they may have matching pairs of codes and/or values. There may be a code/value determined from the assay definition data and a code/value determined from the simulation model. Whenever a code/value for a state determined from the assay definition data is different from a code/value for a state determined from the simulation model, then it may be assumed that the assay definition data was not correctly translated into the control commands that have been sent to the laboratory automation device.

According to an embodiment of the invention, the method further comprises: receiving configuration data of the laboratory automation device, the configuration data containing information about a configuration of the device components within the laboratory automation device; and generating the simulation model from the configuration data and from modelling data for device components.

The configuration data may be stored in a file in the controller and/or may be sent to the software module running the simulation model, when the software module generates the model components in the simulation model. The configuration data may encode an instrument configuration of the laboratory automation device. The instrument configuration may describe how directly controllable device components may be accessed, for example, which ports they use. Such components may include an instrument arm, a turntable, a gripper, a pipette, a sensor tip, a heating device, etc. A directly controllable device component may be a device component having one or more actuators.

Additionally, the configuration data also may encode a device layout, i.e. a configuration of device components in the laboratory automation device. These device components additionally to directly controllable device components may include indirectly controllable or passive device components, such as cartridges with sample tubes, microplates with wells, removable worktables, containers with reagents, etc. The device layout may be at least partially automatically generated by the laboratory automation device and then sent to the controller. For example, sensors may detect positions of specific device components and/or may read barcodes on the device components, which encode their content. These information may be sent by state messages from the laboratory automation device to the controller, which may be triggered in the beginning by the controller. According to an embodiment of the invention, the method further comprises: receiving state messages from the laboratory automation device to the controller, the state messages comprising information about an actual processing state of the device components and/or substances to be processed by the device components. Generally, state messages may be generated by sensors and/or component controllers inside the laboratory automation device. For example, state messages may comprise the content of read barcodes, collision detections between specific device components, a detection of missing reagents, a detection of missing pipette tips, etc. As the control commands, the state messages may be provided in a stream and/or in a series, which indicates an order, in which the state messages have been generated.

From these state messages, on the one hand, the simulation model may be generated by the software module running the simulation model. For example, when the controller requests the device layout from the laboratory automation device, the software module may extract relevant states, such as the actual position, orientation and/or content of device components and updates the values and/or codes for these states in the model components accordingly.

According to an embodiment of the invention, the method further comprises: updating the simulation model based on the actual processing states. It also may be that for specific device components, besides a first state, also subsequent states of model components in the simulation model are determined from the state messages (and not from control commands). For example, when a container with pipette tips is detected in the beginning, in simulation model it may be assumed that all slots are filled with pipette tips. When it is then detected that a specific slot is empty, this information may be updated in the simulation model and, for example, a model component representing the pipette tip not present in reality may be deleted.

According to an embodiment of the invention, the method further comprises: generating a history of desired processing states from the assay definition data and a history of virtual processing states from the determined virtual processing states. Some or all of the desired and virtual processing states may be collected into a timely ordered list. A history of a processing state may be a list, which indicates the change of the processing state over time. For example, the content of a cavity, such as the substances put into the cavity, may be collected over time and a list may be created from this information.

It also may be that desired and/or virtual processing states, in particular those for liquids, are represented as a tree. For example, the root of a tree may be a current liquid that keeps information about the liquid and about operation that created that liquid. Each node of the tree may have one or more child nodes that represent a history of this liquid. A node that represents a mix of two liquids may contain two child nodes. The two child nodes may represent mixed liquids. Those nodes may have child nodes as well, etc. A leave of the tree may represent a source liquid, such as a sample, a reagent, etc.

According to an embodiment of the invention, the method further comprises: comparing the history of the desired processing states with the history of the virtual processing states for deciding, whether the assay procedure was correctly executed. The items of the history may be encoded in numbers and/or codes, which indicate the respective state. All items of the virtual history and the desired history may be compared. In the case, when there is at least one difference, it may be assumed that there was an error in executing the assay procedure.

It has to be noted that the laboratory automation device usually performs the assay procedure for a plurality of samples. For every sample, there may be specific model components (such as wells of a microplate), which are associated with the sample. For each of these samples and/or some or all of the model components associated with the respective sample, a history of associated desired and virtual processing states may be generated. Thus, it may be determined, whether the assay procedure was correctly executed for a sample or not. For example, for every sample, a history of the content of an associated well may be generated.

According to an embodiment of the invention, the assay definition data comprises an ordered list of entries, each entry encoding one or more desired processing states to be reached by the laboratory automation device after the entry has been executed by the laboratory automation device. For example, the assay procedure may comprise steps, such as "pipette sample into well", "pipette specific substance into well", etc. These steps may be encoded into the assay definition data, which may be an XML file. Every entry of the assay definition data may encode the task, to be performed, such as "pipette", "wash", "dilute", "heat", etc., and the one or more components to be processed, such as "sample", "substance A", etc. Such entries also may be seen to encode the desired processing state. For example "pipette sample" also may be interpreted as "sample pipetted into well", which may be seen as the processing state to be reached by the corresponding entry of the assay definition data.

According to an embodiment of the invention, the controller of the laboratory automation device is adapted for transforming the entries of the assay definition data into a program that generates the control commands. It may be that the assay definition data is directly used by the controller to control the laboratory automation device. Every entry of the assay definition data may be transformed into one or more high level commands for controlling the laboratory automation device. These high level commands may be transformed, for example via several steps, into the control commands, which are sent to the laboratory automation device. The list of high level commands may be seen as a program executed by the controller.

According to an embodiment of the invention, the model components of the simulation model comprise one or more (for example two, three-dimensional) virtual objects, which are virtually moved by a simulation engine based on the control commands. Every device component, which is modelled in the simulation model via a model component, may be modelled via one or more virtual objects. These objects may be objects of an objected oriented programming language. The processing states of each virtual object may be encoded with parameters indicative of a processing state, such as one or more 2D or 3D coordinates, a value for a temperature, a value for a liquid level, a value and/or code for a substance contained into the model component, etc. The simulation engine may receive specific control commands, may evaluate them and may change the parameters of the virtual objects accordingly. For example, when the control command "move pipette by 5 cm in x-direction" is received, then the value of the coordinate of the respective virtual object is updated accordingly. In general, processing states of the laboratory automation device may be positions of device components and/or other physical properties.

According to an embodiment of the invention, the model components comprise virtual objects representing substances and/or liquids in the laboratory automating device, which substances and/or liquids are processed by the device components. In a simple case, substances and/or liquids may be encoded with specific values. For example, the content of a well may be encoded with a set of alphanumerical codes, each of which indicates a substance and/or liquid pipetted into the well. However, it also may be possible that a liquid level is encoded as virtual object and/or even a 2D or 3D volume of the substance and/or liquid is represented with a virtual object. This, for example, may be used for a liquid that is pumped through a channel.

According to an embodiment of the invention, the model components comprise one or more virtual actuator objects, which translate a control command into a state change and/or movement of one or more virtual objects. State changes or changes of virtual processing states may include position changes, temperature changes, content changes, etc. For example, motors or more general actuators of the laboratory automation device may be represented by virtual actuator objects, which are supplied with the respective control commands. These actuator objects may contain functions that are adapted for transforming the control commands into state changed of other virtual objects. For example, a heater object, which may receive a control command for being heated to a specific temperature, may change the temperature state of all virtual objects, which have position states inside a volume of the heater object, to the specific temperature.

It also may be that the simulation model has a specific virtual object, which receives all control commands and distribute the control commands to the respective virtual actuator objects. It also has to be noted that virtual actuator objects may have processing states, which are changed by themselves and/or by other virtual actuator objects.

According to an embodiment of the invention, the controller of the laboratory automation device is a computing device separate from the laboratory automation device and the digital control commands are sent via a digital communication line to the laboratory automation device. The digital communication line may be tapped by a computing device executing the method for receiving the control commands and optionally the state messages.

For example, the controller may be a PC, which is interconnected via a digital communication line with the laboratory automation device. The controller may execute control modules, which generate the control commands and may send them via the communication line to the laboratory automation device.

The communication may be based on USB or Ethernet. As an example, the digital control commands and/or the state messages are transmitted via an USB cable or an Ethernet cable between the controller and the laboratory automation device.

According to an embodiment of the invention, a software module for executing the method and comprising the simulation model is executed in the controller of the laboratory automation device. In this case, the control commands and the state messages may be tapped with a sniffer module, which is adapted for monitoring the communication via an interface and/or port via which the controller is connected with the laboratory automation device. In such a way, the monitoring module may be opaque for the other control modules of the controller. The method may be executed in a different task, which has no access to the memory resources of the control modules, which generate the control commands.

According to an embodiment of the invention, a software module for executing the method and comprising the simulation model is executed in an additional computing device different from the controller of the laboratory automation device. The additional computing device may be seen as separate monitoring device. Such a physically separated monitoring device may be more secure than a software module executed in the controller, for example by avoiding to add new risks to the controller.

The monitoring device may tap the communication between the laboratory automation device and its controller. For example, a sniffer module running in the controller may forward the data packets sent between the controller and the laboratory automation device to the monitoring device. In such a way, all control commands and all state messages may be received in the monitoring device.

A further aspect of the invention relates to a computer program for monitoring a laboratory automation device, which, when being executed by a processor, is adapted to carry out the steps of the method as described in the above and in the following. As already mentioned, the computer program may be either executed by the controller itself or by a further computing device.

A further aspect of the invention relates to a computer-readable medium, in which such a computer program is stored. A computer-readable medium may be a floppy disk, a hard disk, an USB (Universal Serial Bus) storage device, a RAM (Random Access Memory), a ROM (Read Only Memory), an EPROM (Erasable Programmable Read Only Memory) or a FLASH memory. A computer-readable medium may also be a data communication network, e.g. the Internet, which allows downloading a program code. In general, the computer-readable medium may be a non-transitory or transitory medium.

A further aspect of the invention relates to a monitoring system for a laboratory automation device, which comprises a monitoring device adapted for receiving the digital control commands and for performing the method as described in the above and in the following.

According to an embodiment of the invention, the system further comprises the laboratory automation device with a plurality of device components. Furthermore, the system may comprise a controller adapted for generating the digital control commands from assay definition data, wherein the device components are controlled by the digital control commands. The monitoring device may be provided by the controller or may be a different physical computing device.

It has to be understood that features of the method as described in the above and in the following may be features of the monitoring system, the computer program and the computer-readable medium as described in the above and in the following and vice versa.

These and other aspects of the invention will be apparent from and elucidated with reference to the embodiments described hereinafter.

BRIEF DESCRIPTION OF THE DRAWINGS

Below, embodiments of the present invention are described in more detail with reference to the attached drawings.

The reference symbols used in the drawings, and their meanings, are listed in summary form in the list of reference symbols. In principle, identical parts are provided with the same reference symbols in the figures.

DETAILED DESCRIPTION OF EXEMPLARY EMBODIMENTS

Figure 1:
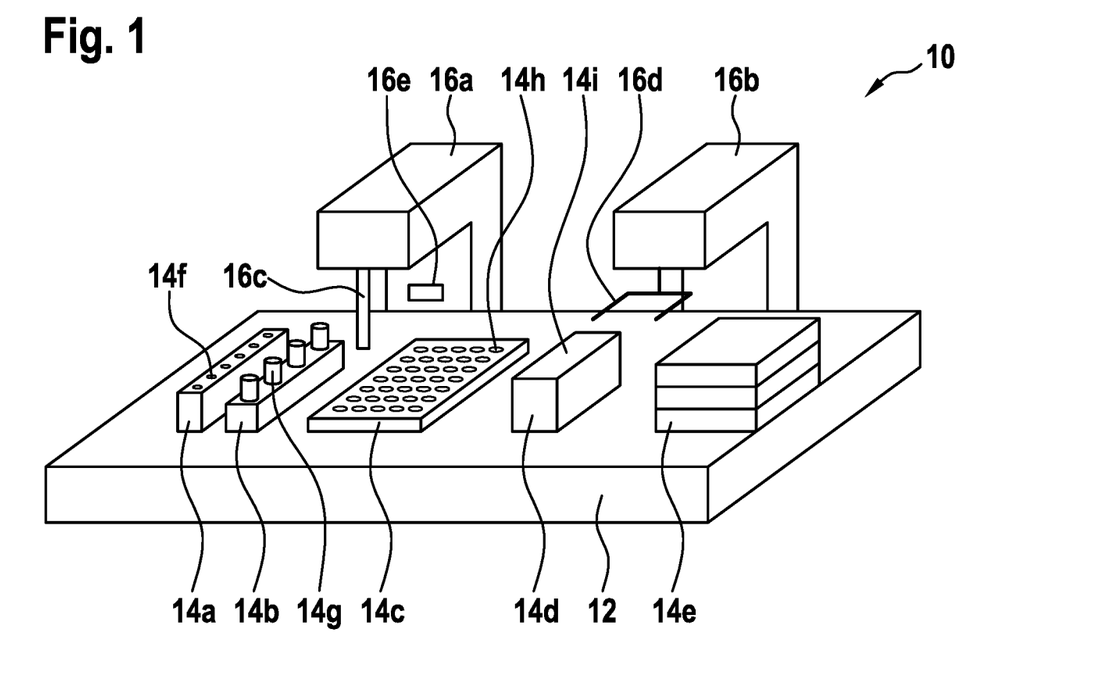
FIG. 1 schematically shows a laboratory automation device.

FIG. 1 shows a laboratory automation device 10, which comprises a workbench 12 onto which several device components 14a to 14e are mountable. The shown examples include a cartridge 14a with pipette tips 14f, a cartridge 14b with test tubes 14g, a microplate 14c with wells 14h, a container 14d containing a reagent 14i and several further microplates 14e.

Furthermore, some controllable device components 16a, 16b are mounted to the workbench 12. A pipette mover 16a comprises a pipette 16c, which may be moved in three dimensions, for example with the aid of motors. With the pipette mover 16a, the pipette 16c may be moved to the pipette tips 14f, which may be stuck on the pipette 16. A sample may be pipetted with the pipette 16c from the test tubes, by being aspirated with a plunger 16e and may be dispensed into a well 14h. Analogously, the reagent 14i may be conveyed into the well 14h. A gripper 16b may comprise a gripper arm 16d, which also may be moved in three dimensions and rotated parallel to the workbench 12. With the gripper 16b, the microplates 14c, 14e may be exchanged and moved into further devices, such as a heater, an optical analysis device, etc.

Figure 2:
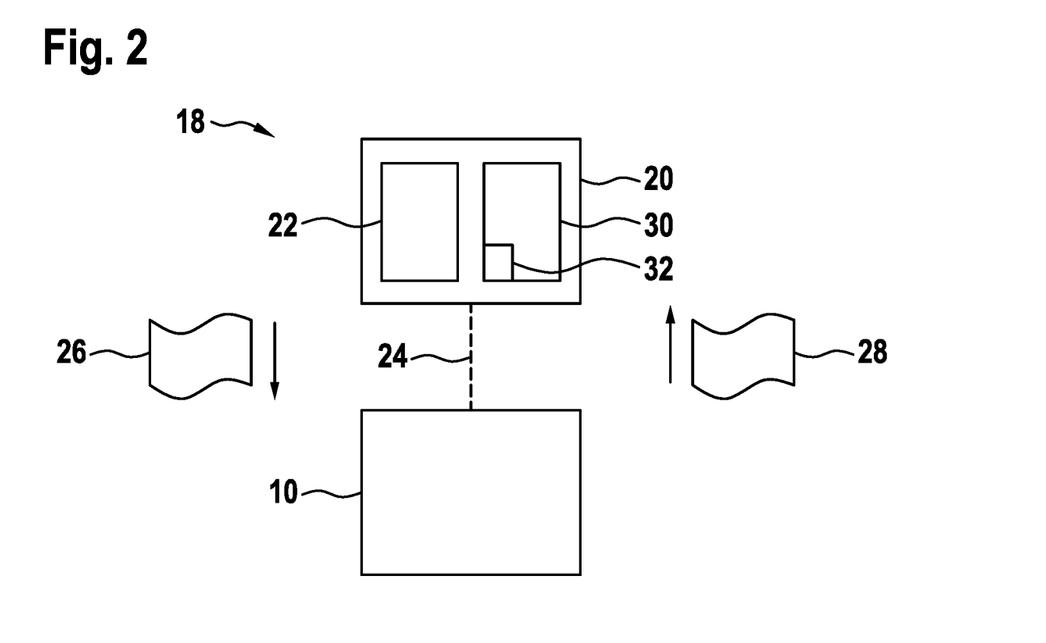
FIG. 2 schematically shows a monitoring system according to an embodiment of the invention.

FIG. 2 shows a monitoring system 18, which comprises a laboratory automation device 10, such as the one shown in FIG. 1, and a controller 20. For example, the controller 20 is a PC or other computing device, in which a control module 22 is run, which performs the control operations of the laboratory automation device 10. The controller 20 and the laboratory automation device 10 are interconnected with a communication line 24, such as an USB cable or an Ethernet cable.

The control module 22 generates digital control commands 26, such as firmware commands, which are sent via the communication line 24 to the laboratory automation device 10. Digital control commands 26 may be alphanumerical codes, which are packed into data packets, which are exchanged between the controller 20 and the laboratory automation device 10. On the side of the laboratory automation device 10, the digital control commands 26 are received by device components 14, 16 with a device controller, such as motors for the pipette mover 16*a* and the gripper 16*b* and processed. These device controllers and/or further sensors in the laboratory automation device 10 generate state messages 28, which, analogously to the control commands 26, may be alphanumerical codes and/or may be packed into data packets, which are sent via the communication line 24 to the controller 20.

FIG. 2 furthermore shows a monitoring module 30, which as described above and below, monitors the operation of the system 18. The monitoring module 30 may be a software module that as the control module 22 is run in the controller 20. The monitoring taps the communication between the control module 22 and the laboratory automation device 10. This may be done with a sniffer module 32, which may be a part of the monitoring module 30. The sniffer module 32 may directly access the data packets to and from the communication line 24 and/or may extract the control commands 26 and the state messages 28 from the data packets.

Figure 3:
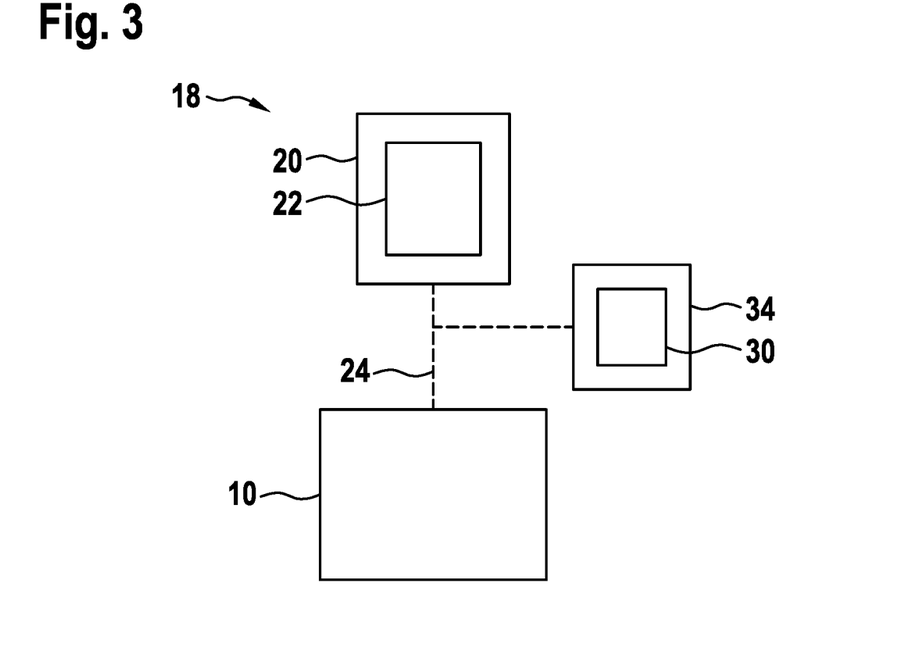
FIG. 3 schematically shows a monitoring system according to an embodiment of the invention.

FIG. 3 shows a further embodiment of a monitoring system 18, which comprises a separate monitoring device 34. The separate monitoring device 34 may be a computing device, such as a further PC, an embedded device, etc., which has hardware (such as a processor, memory, etc.) of its own with respect to the controller 20. The monitoring module 30 is executed in the separate monitoring device 34 and an interference between the monitoring module 30 and the control module 22 may be lower in this case.

The separate monitoring device 34 may tap the communication between the controller 20 and/or the control module 22 and the laboratory automation device 10. For example, a sniffer module 32 running in the controller 20 may access the data packets sent between the controller 20 and the laboratory automation device 10 and may send them to the separate monitoring device 34.

Figure 4:
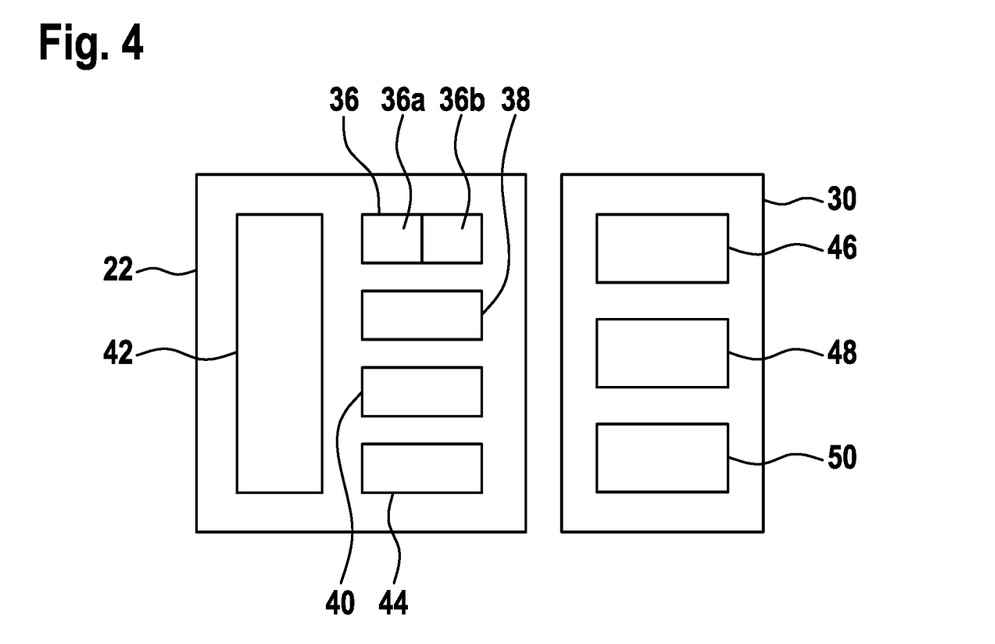
FIG. 4 schematically shows modules of the monitoring system of FIG. 3.

FIG. 4 shows a functional view of the control module 22 and the monitoring module 30.

The control module 22 comprises configuration data 36, which may be composed of instrument configuration data 36*a* and device layout data 36*b*. The instrument configuration data 36*a* may encode a software and/or hardware configuration of controllable device components 16. The instrument configuration data 36*a* may have been downloaded from the laboratory automation device 10. The device layout data 36*b* may encode a configuration and/or layout of the device components 14, 16, such as which are present, what properties they have and/or how they are spatially related to each other. The device layout data 36*b* may have been generated from state messages from the laboratory automation device 10, which may be adapted for scanning its device layout. For example, a barcode scanner may be adapted for determining, which kind of microplates 14*c* are present.

Alternatively, the device layout data 36 may be created with an editor and/or may be an XML file, which is then optionally updated with state massages.

Furthermore, the control module 22 comprises assay definition data 38, which basically comprises a list of entries defining the steps of an assay procedure to be performed by the laboratory automation device. The assay definition data 38 will be described below in more detail with respect to FIG. 5. As a simple example, the assay definition data 38 may include entries, which encode assay procedure steps as "pipette sample into well", "dilute sample in well", etc.

The control module 22 is adapted for transforming the entries of the assay definition data 38 into a program 40 that generates the control commands 26. To this end, the control module 22 may comprise a translation and execution module 42, which, comparable to a compiler, is adapted for translating the entries of the assay definition data into commands of the program 40. The module 42 may use the configuration data 36 for performing this task. For example, the configuration of the pipette arm 16*a* and the cartridge 14*a* with test tubes 14, which also may encode the position of the test tubes 14*f*, may be translated into commands for movements of the pipette 16*c* as well as an aspiration and dispensing of liquids at the desired positions.

The program 40 may then be executed by the translation and execution module 42, which results in the generation of the control commands 26. During execution, the program 40 also may receive state messages 28 from the laboratory automation device 10 and may react thereupon. It has to be noted that the task of generation of the control commands 26 may be performed in several layers in the control modules. For example, the module 42 may generate high level commands, which are further translated into the control commands 24 by drivers 44.

FIG. 4 furthermore shows that the monitoring module 30 comprises a simulation model 46, which is used for monitoring the system 18. The simulation model 46 is created from the configuration data 36, modelling data 48 and optionally further data, such as state messages 28 from the laboratory automation device 10. As will be described with respect to FIG. 6 in more detail, the simulation model is composed of model components that simulate some or all of the device components 14, 16 of the laboratory automation device 10.

For example, the initialisation and evaluation module 50 may read the configuration data 36, may determine the device components 14, 16 actually present and may generate model components for these device components 14, 16 in the simulation model 46 based on the modelling data 48. For example, the modelling data 48 may comprise information about the layout, spatial extension, movement abilities, etc. of the device components 14, 16 that are not stored in the configuration data 36.

After the generation of the simulation model 46, the initialisation and evaluation module 50 may inject control commands 26 into the simulation model 46, which is updated based into these control commands 26 and performs virtual processing state changes.

The module 50 is also adapted for determining desired processing states of the device components 14, 16 from the assay definition data 38. By comparing the desired processing states with virtual processing states of the simulation model 46, the module 50 is adapted for monitoring the system 18, i.e. whether the assay procedure as defined by the assay definition data 38 is performed by the laboratory automation device 10 in the intended way.

It has to be noted that the modules shown in FIG. 4 all may be based on files stored in the computing devices 20 and/or 34. The data 36, 38, 50 also may be stored in files, such as XML files.

Figure 5:
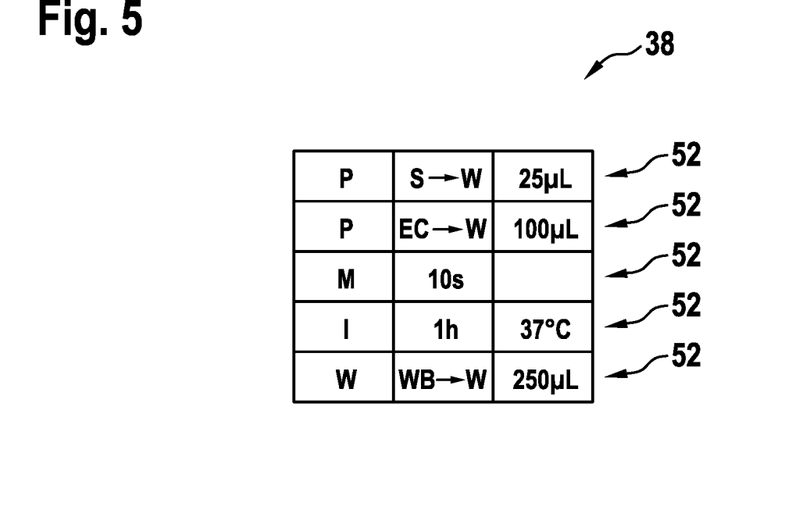
FIG. 5 schematically illustrates assay definition data used in the monitoring system of FIG. 3.

FIG. 5 schematically illustrates an example of assay definition data 38. In FIG. 5, the assay definition data 38 is an ordered list of entries, each of which encodes a step of an assay protocol or assay procedure.

In general, for example to test a patient for a specific disease, a sample of his blood, urine, stool, etc. is taken and analyzed by means of a bio-chemical procedure. Such a procedure comprises various operations/steps like adding substances, incubating, separating (for example with a centrifuge), etc. and a measurement process which quantitatively or qualitatively measures the amount or presence of a substance indicating the specific disease. Such an analysis is usually called an assay. The sequence of the steps to be executed may be called assay protocol or assay procedure and is encoded in the assay definition data 38.

An example for an assay procedure is shown in the following table.

1.) Pipette 25 µL of each sample into a well of the microplate.
2.) Pipette 100 µL of Enzyme Conjugate into each well.
3.) Mix for 10 seconds.
4.) Incubate 1 h at 37° C.
5.) Wash microplate 3 × with 250 µL of diluted Wash Buffer.
6.) Pipette 100 µL of Substrate Solution into each well.
7.) Incubate 15 min at room temperature (18-25° C.).
8.) Adding 100 µL of TMB Stop Solution into each well.
9.) Mix for 10 seconds.
10.) Measure optical density of solution in well with a photometer at 450 nm.

In FIG. 5, the first 5 steps from the above table are encoded into the entries 52. As shown, each entry comprises a task "P", "M", etc. to be executed by the laboratory automation device 10 and optionally additional information, necessary for the task.

On the one hand, the control module 22 is adapted for transforming these tasks into control commands 26 for the laboratory automation device 10. For example, each task and its optional information may be transformed into commands of the program 40, which is then executed in the control module 22.

On the other hand, the monitoring module 30 is adapted for generating desired processing states of the laboratory automation device 10 from the entries 53 of the assay definition data 38. The initialisation and evaluation module 50 may read the assay definition data 38 and may determine the desired processing state from the data of each entry 52. For example, after the first entry, a well associated with a sample contains 25 µL of the sample. After the second step, the well associated with the sample contains additionally 100 µL of the enzyme conjugate, etc. It may be possible that the desired processing states are directly encoded in the assay definition data 38 or that they are generated from the assay definition data 38 and stored in an additional table.

Figure 6:
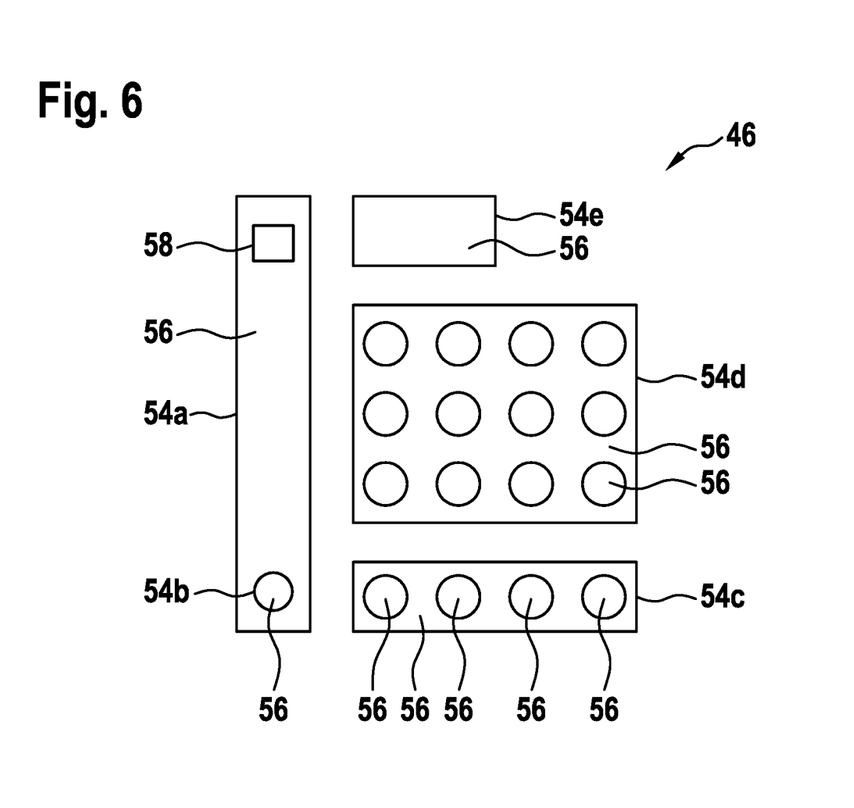
FIG. 6 schematically illustrates a simulation model used in the monitoring system of FIG. 3.

FIG. 6 schematically shows an embodiment of the simulation model 46. The simulation model 46 comprises model components 54, each of which represents device components 14, 16 of the laboratory automation device 10. In the example of FIG. 6, there is a model component 54a for the pipette mover 16a, a model component 54b for the pipette 16c, a model component 54c for the cartridge 14b with test tubes 14g, a model component 54d for a microplate 14c with wells 14h and a model component 54e for a container 14d containing a reagent 14i.

Each of the model components 54 may be virtual objects 56 in a simulation engine, which may be part of the monitoring module 30 and/or may contain further virtual objects 56, which, for example, may represent the test tubes 14g and the wells 14h.

The model components 54a and/or virtual objects 56 may be objects of an object-oriented programming language and/or may include variables that encode processing states of the device components 14, 16, which are simulated with the simulation model 46. In the present example, the model component 54a for the pipette mover 16a may comprise variables encoding the positions of the motors of the pipette mover 16a. The model component 54b of the pipette 16c may comprise variables encoding a two-dimensional position of the pipette tip. In the simulation model shown in FIG. 6, the positions of the modelled device components 14, 16 are provided in 2D coordinates. Thus, a relative position of the simulated pipette 54b with respect to the simulated test tubes may be determined, which may be enough for determining, whether, in simulation, the pipette 54b is lowered into one of the test tubes, the wells or a container, etc.

It has to be noted that it is also possible that the simulation model 46 is based on 3D data, i.e. all positions, movements and volumes may be simulated with respect to three spatial dimensions.

A further possible processing state that may be stored in variables of the model components 54 and/or virtual objects 56 may be the content of one of the wells of the microplates. For example, the content may be encoded in a set of alphanumeric codes, each of which represents a specific substance that was pipetted into the respective well. The alphanumeric codes additionally may encode, whether the content was heated, stirred, incubated, etc.

Also the model component for the pipette 54b may comprise such a variable, which encodes its current content.

Some of the model components 54 also may comprise actuator objects 58 that may be special virtual objects 56 that are adapted for processing control commands 26 for the laboratory automation device 10. For example, in FIG. 5, an actuator object 58 is shown, which receives control commands 26 associated with the simulated pipette 54b. The actuator object 58 may translate the control commands 26 into virtual movements of the simulated pipette 54, i.e. may update the variables storing the position of the simulated pipette 54b. Furthermore, when commands 26 are received that control a lowering of the pipette and an aspiration, the variable of the simulated pipette 54b encoding the content of the simulated pipette 54b may be set to the content of the simulated component that is below the simulated pipette 54b. Analogously, when control commands 26 are received that dispense the simulated pipette 54b, the content of the pipette 54b may be added to the content of the simulated component below the pipette 54b.

In general, an actuator object 58 may be adapted for translating control commands 26 into virtual processing state changes of the model components 56 and/or virtual objects 58 of the simulation model.

Figure 7:
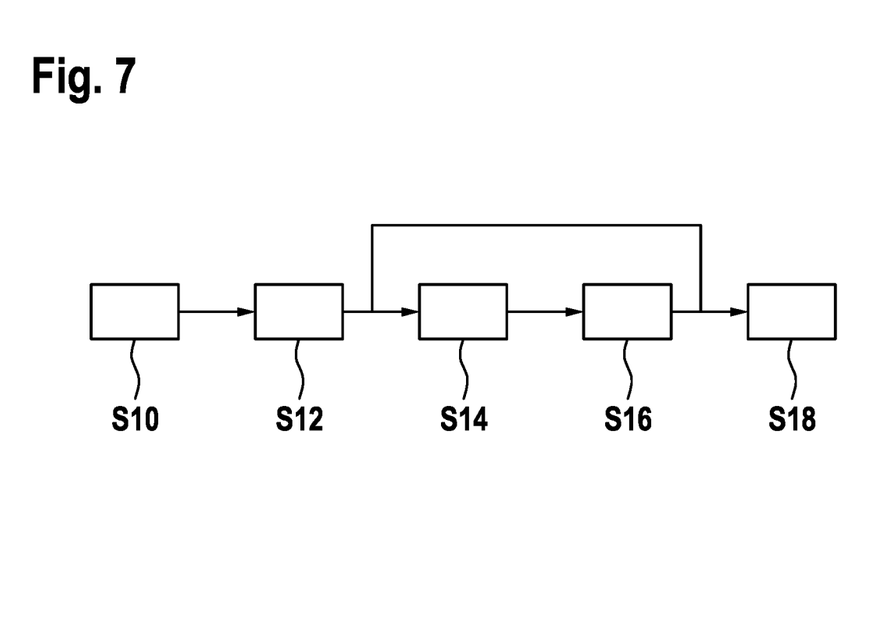
FIG. 7 shows a flow diagram for a monitoring method according to an embodiment of the invention.

FIG. 7 shows a flow diagram for a method that may be performed by the monitoring module 32 and/or the monitoring device 34.

In step S10, the simulation model 46 is initialised. The initialization and evaluation module 52 receives the configuration data 36 of the laboratory automation device 10 from the control module 22, for example by sending a corresponding request or by reading a corresponding file. From the configuration data, model components 54 are created in the simulation model 46. For each device component 14, 16 that should be simulated by the simulation model 46, a generic model component 54 is taken from the modelling data 48, which generic model component 54 is updated with further data from the configuration data. For example, the positions and/or extensions of the respective device components are updated in the generic model components.

In general, the simulation model 46 may be generated from the configuration data 36 and from modelling data 48 for device components 14, 16. The instrument configuration data 36a may be used for generating model components 54 for controllable device components 16. Device layout data 36 may be used for generating model components 54 for device components 14, 16.

It may be that specific control commands 26 from the control module 22 indicate that new assay procedure to be executed. These control commands may start the initialization of the simulation model 46.

It also may be that such control commands 26 result in state messages 28 generated by the laboratory automaton device 10, which contain further information of the configuration of the device components, such as their actual position. Furthermore, specific initial processing states of device components 14, 16 may be contained in these state messages, such as an actual content of one of the device components 14, 16. For example, a barcode reader may read a code on a container and/or a test tube and/or may generate a state message, which indicates the content of the container and/or test tube.

In step S12, the initialization and evaluation module 52 generates a history of desired processing states from the assay definition data 38. The initialization and evaluation module 52 may receive the assay definition data 38 from the control module 22, for example by sending a corresponding request or by reading a corresponding file.

Figure 8:
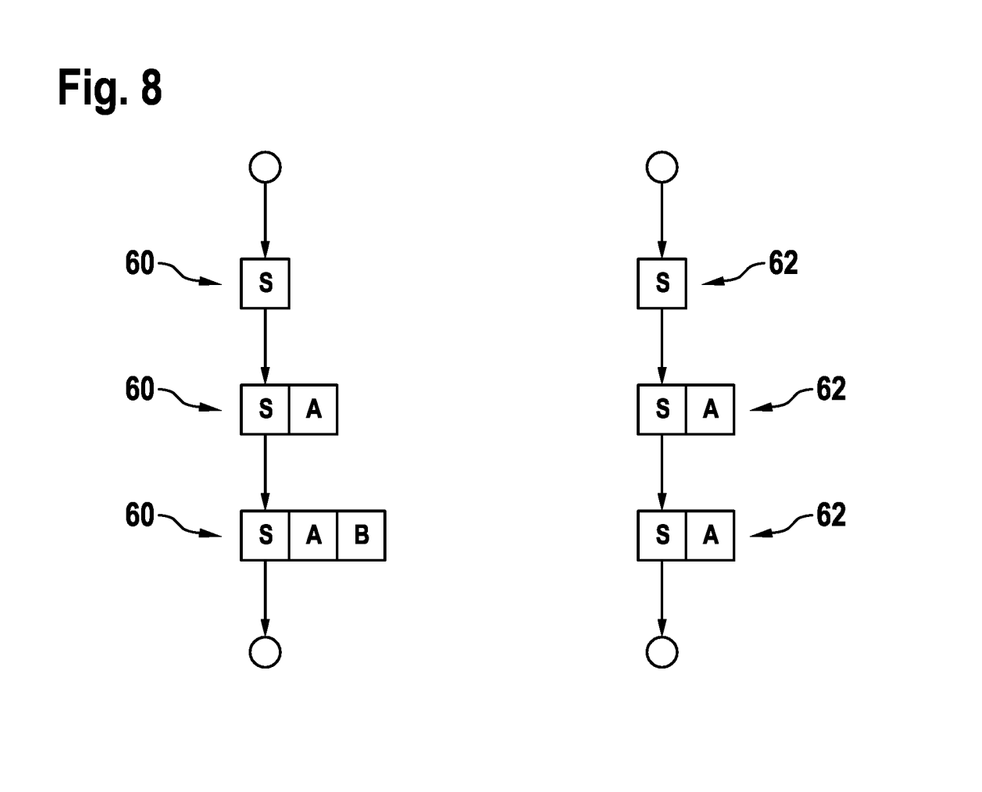
FIG. 8 schematically illustrates histories of processing states that may be generated with the method of FIG. 7.

FIG. 8 shows an example with such desired processing states 60. In particular, in FIG. 8, a history of desired processing states 60 is shown on the left hand side. In general, each entry 52 of the assay definition data may encode one or more desired processing states 60, which may be reached by the laboratory automation device 10 after the entry 52 has been executed by the laboratory automation device 10, for example by being translated into commands of the program 40 as described above.

For example, as shown in FIG. 8, the assay definition data 38 may have entries 52, which encode that a sample, a reagent A and a reagent B are pipetted into the well and that the well is washed afterwards. FIG. 8 shows a history of the processing state, which encodes the actual content of the well, which is associated with the sample. In the beginning, the well is empty. After the first assay procedure step, it contains the sample (encoded with "S"). After the second assay procedure step, it contains the sample and reagent A (encoded with "S" and "A"). After the third assay procedure step, it contains the sample, reagent A and reagent B (encoded with "S", "A" and "B"). After, the fourth assay procedure step, i.e. the washing, the well is again empty.

It has to be noted that step S12 may be performed later, earlier or in parallel to the following steps.

In step S14, the simulation model 46 is updated. The monitoring module 30 receiving the control commands 26, which are generated by the control module 22 during the execution of the assay procedure, and the control commands 26 are inputted into the simulation model 46, which is then updated by simulating state changes of the device components 14, 16 based on the control commands 26. It may be that only a subset of the control commands 26, for example only those intended to specific device components 14, 16 are input in the simulation model 46.

As already mentioned, the model components 54 of the simulation model comprise one or more virtual actuator objects 58, which translate the control commands 26 into state changes of the model components 54. For example, the model components may comprise two- or three-dimensional virtual objects 56 with 2D- or 3D-positions as virtual processing states, which are virtually moved by a simulation engine based on the control commands 26. As described above, there also may be processing states such as temperature, incubation, etc., which also may be represented by virtual processing states.

It also may be that liquids in cavities, such as wells or channels, are simulated as two- or three-dimensional virtual objects 56. However, it also may be possible that only liquid level or a content of a cavity is tracked as virtual processing state. A liquid level may be calculated from a volume of the liquid dispensed into the cavity and a known spatial extension of the cavity.

Optionally, it also may be that state messages 28 from the laboratory automation device 10, which are sent to the controller 20, are used for updating the simulation model 46. In general, the state messages 28 may comprise information about an actual processing state of the device components 14, 16 and/or substances to be processed by the device components 14, 16. For example, the laboratory automation device 10 may send actual positions and/or orientations of device components 14, 16 to the control module 22.

In this case, the simulation model 46 also may be updated based actual processing states determined from state messages 28. For example, this may be done for model components 56, which are not simulated based on control commands.

In step S16, virtual processing states 62 are determined from the updated simulation model 46. FIG. 8 shows on the right hand side an example with a history of virtual processing states 62, which is generated from the determined virtual processing states that are stored in the model components 54 and/or virtual objects 56.

The next part of the history may be generated, when the end of an assay procedure step is reached and/or whenever the virtual processing states change.

In the example of FIG. 8, the history of virtual processing states 62 on the right hand side differs from the history of desired processing states, since in the third step of the assay procedure, an error occurred. Reagent B was not dispensed into the well of the sample. A reason for this may be that there has been a problem in the translation from the assay definition data 38 to the control commands 26. This translation may be performed in various stages by various software components 42 and/or drivers 44, which may result in unexpected side effects.

The steps S14 and S16 may be repeated until the assay procedure is finished by the laboratory automation device 10. This also may be indicated by specific control commands 26 and/or state messages 28.

In step S18, the initialization and evaluation module 50 compares the two histories of processing states 60, 62. Every element of the history of the desired processing states 60 is compared with the corresponding element of the history of the virtual processing states 62 for deciding, whether the assay procedure was correctly executed. When at least one of these elements is different, it may be assumed that an error occurred. For example, in FIG. 8, the variable storing the content of the processing states 60, 62 differs after the third processing step. Thus, it may be assumed that something went wrong and a corresponding warning may be put out by the monitoring module 30.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practising the claimed invention, from a study of the drawings, the disclosure, and the appended claims. In the claims, the word "comprising" does not exclude other elements or steps, and the indefinite article "a" or "an" does not exclude a plurality. A single processor or controller or other unit may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A method for monitoring a laboratory automation device, the method comprising:
   receiving control commands;
   inputting the control commands into a simulation model of the laboratory automation device, wherein the laboratory automation device comprises a plurality of device components, which are controlled by the control commands, wherein the control commands are generated by a controller of the laboratory automation device from assay definition data defining an assay procedure for the laboratory automation, and wherein the simulation model comprises model components for at least some of the device components;
   updating the simulation model by simulating state changes of the device components based on the control commands, wherein the model components of the simulation model comprise one or more virtual objects, which are virtually moved by a simulation engine based on the control commands, the virtual objects representing liquids in the laboratory automating device, which liquids are processed by the device components;
   determining a virtual liquid processing state of the laboratory automation device from the updated simulation model;
   determining a desired liquid processing state of the laboratory automation device from the assay definition data, wherein the virtual liquid processing state and the desired liquid processing state are represented as trees, and wherein the assay definition data comprises an ordered list of entries, each entry encoding one or more desired liquid processing states to be reached by the laboratory automation device after the entry has been executed by the laboratory automation device;
   and comparing the desired liquid processing state with the virtual liquid processing state for deciding, whether the assay procedure was correctly executed, when a code for a desired liquid processing state determined from the assay definition data is different from a code for a virtual liquid processing state determined from the simulation model, it is assumed that the assay definition data was not correctly translated into the control commands that have been sent to the laboratory automation device.

2. The method of claim 1, further comprising:
   receiving configuration data of the laboratory automation device, the configuration data containing information about a configuration of the device components within the laboratory automation device;
   generating the simulation model from the configuration data and from modelling data for device components.

3. The method of claim 2, further comprising:
   receiving state messages from the laboratory automation device to the controller, the state messages comprising information about an actual liquid processing state of the device components and/or liquids to be processed by the device components.

4. The method of claim 3, further comprising:
   updating the simulation model based on the actual liquid processing states.

5. The method of claim 1, further comprising:
   generating a history of desired liquid processing states from the assay definition data and a history of virtual liquid processing states from the determined virtual liquid processing states;
   comparing the history of the desired liquid processing states with the history of the virtual liquid processing states for deciding, whether the assay procedure was correctly executed.

6. The method of claim 1,
   wherein the controller of the laboratory automation device is adapted for transforming the entries of the assay definition data into a program that generates the control commands.

7. The method of claim 1,
   wherein the model components comprise one or more virtual actuator objects, which translate a control command into a state change of one or more virtual objects.

8. The method of claim 1,
   wherein the device components comprise at least one of an instrument arm, a turntable, a gripper, a pipette, a sensor tip, a plate with wells, a cavity, a well, a plunger, a heating device.

9. The method of claim 1,
   wherein the controller of the laboratory automation device is a computing device separate from the laboratory automation device and the digital control commands are sent via a digital communication line to the laboratory automation device;
   wherein the digital communication line is tapped by a computing device executing the method.

10. The method of claim 1,
    wherein a software module for executing the method and comprising the simulation model is executed in the controller of the laboratory automation device; or
    wherein a software module for executing the method and comprising the simulation model is executed in an additional computing device different from the controller of the laboratory automation device.

11. A computer program for monitoring a laboratory automation device, wherein the computer program, when being executed by a processor, is adapted to carry out the following steps:
    receiving the control commands;
    inputting the control commands into a simulation model of the laboratory automation device, wherein the laboratory automation device comprises a plurality of device components, which are controlled by the control commands, wherein the control commands are generated by a controller of the laboratory automation device from assay definition data defining an assay procedure for the laboratory automation, and wherein the simulation model comprises model components for at least some of the device components;

updating the simulation model by simulating state changes of the device components based on the control commands, wherein the model components of the simulation model comprise one or more virtual objects, which are virtually moved by a simulation engine based on the control commands, the virtual objects representing liquids in the laboratory automating device, which liquids are processed by the device components;

determining a virtual liquid processing state of the laboratory automation device from the updated simulation model;

determining a desired liquid processing state of the laboratory automation device from the assay definition data, wherein the virtual liquid processing state and the desired liquid processing state are represented as trees, and wherein the assay definition data comprises an ordered list of entries, each entry encoding one or more desired liquid processing states to be reached by the laboratory automation device after the entry has been executed by the laboratory automation device;

and comparing the desired liquid processing state with the virtual liquid processing state for deciding, whether the assay procedure was correctly executed, when a code for a desired liquid processing state determined from the assay definition data is different from a code for a virtual liquid processing state determined from the simulation model, it is assumed that the assay definition data was not correctly translated into the control commands that have been sent to the laboratory automation device.

12. A computer-readable medium, in which a computer program for monitoring a laboratory automation device, wherein the computer program, when being executed by a processor, is adapted to carry out the following steps:

receiving the control commands;

inputting the control commands into a simulation model of the laboratory automation device, wherein the laboratory automation device comprises a plurality of device components, which are controlled by the control commands, wherein the control commands are generated by a controller of the laboratory automation device from assay definition data defining an assay procedure for the laboratory automation, and wherein the simulation model comprises model components for at least some of the device components;

updating the simulation model by simulating state changes of the device components based on the control commands, wherein the model components of the simulation model comprise one or more virtual objects, which are virtually moved by a simulation engine based on the control commands, the virtual objects representing liquids in the laboratory automating device, which liquids are processed by the device components;

determining a virtual liquid processing state of the laboratory automation device from the updated simulation model;

determining a desired liquid processing state of the laboratory automation device from the assay definition data, wherein the virtual liquid processing state and the desired liquid processing state are represented as trees, and wherein the assay definition data comprises an ordered list of entries, each entry encoding one or more desired liquid processing states to be reached by the laboratory automation device after the entry has been executed by the laboratory automation device;

and comparing the desired liquid processing state with the virtual liquid processing state for deciding, whether the assay procedure was correctly executed, when a code for a desired liquid processing state determined from the assay definition data is different from a code for a virtual liquid processing state determined from the simulation model, it is assumed that the assay definition data was not correctly translated into the control commands that have been sent to the laboratory automation device.

13. A monitoring system for a laboratory automation device, the system comprising:

a laboratory automation device with a plurality of device components;

a controller adapted for generating digital control commands from assay definition data defining an assay procedure for the laboratory automation device, wherein the device components are controlled by the digital control commands; and a monitoring device adapted for receiving the digital control commands and for performing the following steps:

receiving the control commands;

inputting the control commands into a simulation model of the laboratory automation device, wherein the laboratory automation device comprises a plurality of device components, which are controlled by the control commands, wherein the control commands are generated by a controller of the laboratory automation device from assay definition data defining an assay procedure for the laboratory automation, and wherein the simulation model comprises model components for at least some of the device components;

updating the simulation model by simulating state changes of the device components based on the control commands, wherein the model components of the simulation model comprise one or more virtual objects, which are virtually moved by a simulation engine based on the control commands, the virtual objects representing liquids in the laboratory automating device, which liquids are processed by the device components;

determining a virtual liquid processing state of the laboratory automation device from the updated simulation model;

determining a desired liquid processing state of the laboratory automation device from the assay definition data, wherein the virtual liquid processing state and the desired liquid processing state are represented as trees, and wherein the assay definition data comprises an ordered list of entries, each entry encoding one or more desired liquid processing states to be reached by the laboratory automation device after the entry has been executed by the laboratory automation device;

and comparing the desired liquid processing state with the virtual liquid processing state for deciding, whether the assay procedure was correctly executed, when a code for a desired liquid processing state determined from the assay definition data is different from a code for a virtual liquid processing state determined from the simulation model, it is assumed that the assay definition data was not correctly translated into the control commands that have been sent to the laboratory automation device.

14. The method of claim 1, wherein one of the trees comprises a root that represents a first of the liquids, and wherein the root comprises information about the first liquid and information about an operation that created the first liquid.

15. The method of claim 1, wherein one of the trees comprises a node that represents a history of the liquids.

16. The method of claim 1, wherein one of the trees comprises a node that represents a mix of two of the liquids, and wherein the node comprises two child nodes.

17. The method of claim 1, wherein a leaf of one of the trees represents a source liquid, and wherein the source liquid comprises a sample or a reagent.

18. The method of claim 1, wherein the virtual liquid processing state, the desired liquid processing state, or both comprises parameters, and wherein the parameters comprise 2D or 3D coordinates.

19. The method of claim 1, wherein the virtual liquid processing state, the desired liquid processing state, or both comprises parameters, and wherein the parameters a value for temperature of the liquids.

20. The method of claim 1, wherein the virtual liquid processing state, the desired liquid processing state, or both comprises parameters, and wherein the parameters a value for a level of the liquids.

* * * * *

UNITED STATES PATENT AND TRADEMARK OFFICE
CERTIFICATE OF CORRECTION

PATENT NO. : 11,630,117 B2  
APPLICATION NO. : 16/213787  
DATED : April 18, 2023  
INVENTOR(S) : Leboudec Page 1 of 1

It is certified that error appears in the above-identified patent and that said Letters Patent is hereby corrected as shown below:

On the Title Page

Item (72), Under Inventor, "Zurich (CH)" should be --Zuerich (CH)--  
Item (73), Under Assignee, "Switzerland (CH)" should be --Maennedorf (CH)--

Signed and Sealed this  
Twenty-third Day of May, 2023

Katherine Kelly Vidal  
*Director of the United States Patent and Trademark Office*